US011439698B2

(12) United States Patent
Hu

(10) Patent No.: US 11,439,698 B2
(45) Date of Patent: Sep. 13, 2022

(54) TOXOID PREPARATION AND USES THEREOF

(71) Applicant: Arytha Biosciences, LLC, San Diego, CA (US)

(72) Inventor: Che-Ming Jack Hu, Taipei (TW)

(73) Assignee: Arytha Biosciences, LLC, San Diego, CA (US)

( * ) Notice: Subject to any disclaimer, the term of this patent is extended or adjusted under 35 U.S.C. 154(b) by 0 days.

(21) Appl. No.: 15/679,096

(22) Filed: Aug. 16, 2017

(65) Prior Publication Data

US 2017/0368160 A1 Dec. 28, 2017

Related U.S. Application Data

(63) Continuation of application No. 15/100,273, filed as application No. PCT/US2014/067688 on Nov. 26, 2014, now abandoned.

(60) Provisional application No. 61/910,861, filed on Dec. 2, 2013.

(51) Int. Cl.
| | |
|---|---|
| *A61K 39/00* | (2006.01) |
| *A61K 39/02* | (2006.01) |
| *A61K 39/085* | (2006.01) |
| *A61K 39/112* | (2006.01) |
| *A61K 9/16* | (2006.01) |

(52) U.S. Cl.
CPC ............ *A61K 39/107* (2013.01); *A61K 9/16* (2013.01); *A61K 39/0283* (2013.01); *A61K 39/085* (2013.01); *A61K 2039/6018* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 4,891,208 | A * | 1/1990 | Janoff | A61K 9/1271 |
| | | | | 264/4.1 |
| 5,088,499 | A * | 2/1992 | Unger | A61K 9/1277 |
| | | | | 424/44 |
| 5,653,999 | A | 8/1997 | Gaudreault et al. | |
| 6,395,029 | B1 | 5/2002 | Levy | |
| 7,514,267 | B1 * | 4/2009 | Lopez | C12Q 1/18 |
| | | | | 435/7.1 |
| 10,098,839 | B2 | 10/2018 | Zhang | |
| 10,285,952 | B2 | 5/2019 | Zhang | |
| 2004/0110695 | A1 | 6/2004 | Dobbie | |
| 2005/0118275 | A1 | 6/2005 | O'Hagan | |
| 2005/0266512 | A1 * | 12/2005 | Buckley | C12Q 1/37 |
| | | | | 435/23 |
| 2007/0243137 | A1 | 10/2007 | Hainfeld et al. | |
| 2009/0274630 | A1 | 11/2009 | Huang | |
| 2010/0021503 | A1 | 1/2010 | Denoel et al. | |
| 2010/0055167 | A1 | 3/2010 | Zhang et al. | |
| 2011/0280930 | A1 * | 11/2011 | Batista | A61K 39/39 |
| | | | | 424/450 |
| 2013/0071326 | A1 | 3/2013 | Martinez et al. | |
| 2013/0071329 | A1 | 3/2013 | Ferrari et al. | |
| 2013/0337066 | A1 | 12/2013 | Zhang et al. | |
| 2015/0157570 | A1 | 6/2015 | Babiychuk et al. | |
| 2016/0136106 | A1 | 5/2016 | Zhang et al. | |
| 2017/0274059 | A1 | 9/2017 | Zhang et al. | |
| 2018/0085320 | A1 | 3/2018 | Zhang et al. | |
| 2018/0140558 | A1 | 4/2018 | Zhang et al. | |
| 2018/0153821 | A1 | 6/2018 | Zhang et al. | |
| 2018/0169027 | A1 | 6/2018 | Zhang et al. | |

FOREIGN PATENT DOCUMENTS

| | | | |
|---|---|---|---|
| CN | 1798548 A | 7/2006 | |
| GB | 2482069 A | 1/2012 | |
| WO | 2005020964 A1 | 3/2005 | |
| WO | 2010014081 A1 | 2/2010 | |
| WO | 2010070620 A1 | 6/2010 | |
| WO | 2011002239 A2 | 1/2011 | |
| WO | 2011/116219 A1 | 9/2011 | |
| WO | 2011116219 A1 | 9/2011 | |
| WO | WO-2012095660 A2 * | 7/2012 | ........... C12Q 1/6869 |
| WO | 2013052167 A2 | 4/2013 | |
| WO | 2017087897 A1 | 5/2017 | |
| WO | 2017/216282 A1 | 12/2017 | |
| WO | 2018/158375 A1 | 9/2018 | |

OTHER PUBLICATIONS

Petrov et al. 1992 (Toxicity and Immunogenicity of Neisseria meningitidis Lipopolysaccharide Incorporated into Liposomes; Infection and Immunity 60(9): 3897-3903). (Year: 1992).*

Fujii et al. 2013 (In vitro evolution of a-hemolysin using a liposome display; PNAS 110(42): 16796-16801) (Year: 2013).*

Bakas et al. 1996 (Reversible Adsorption and Nonreversible insertion of *Escherichia coli* a-hemolysin into lipid bilayers; Biophysical Journal 71: 1869-1876). (Year: 1996).*

Valeva et al. 2006 (Evidence That Clustered Phosphocholine Head Groups Serve as Sites for Binding and Assembly of an Oligomeric Protein Pore; The Journal Of Biological Chemistry; vol. 281, No. 36, pp. 26014-26021). (Year: 2006).*

Colas et al. 2007 (Microscopical investigations of nisin-loaded nanoliposomes prepared by Mozafari method and their bacterial targeting; Micron 38:841-847). (Year: 2007).*

Edwards et al. 2006 (Analysis of liposomes; Talanta 68:1432-1441) (Year: 2006).*

(Continued)

*Primary Examiner* — Mary Maille Lyons
(74) *Attorney, Agent, or Firm* — Rimon, P.C.

(57) ABSTRACT

The present invention relates to toxoid preparations comprising a non-disrupted and/or a non-denatured toxin associated with a particulate vector that minimizes or precludes said toxin from inflicting damage at an action site of said toxin. The present invention also relates to immunogenic compositions or vaccines comprising the toxoid preparations, and the methods of using the toxoid preparations, immunogenic compositions or vaccines.

7 Claims, 3 Drawing Sheets

(56) References Cited

OTHER PUBLICATIONS

Figure 1:
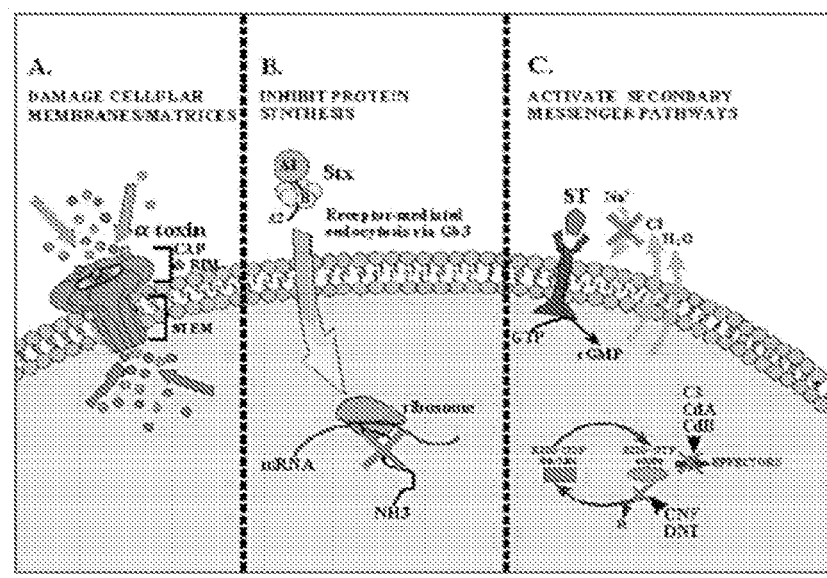

Mouhat et al. 2004 (Diversity of folds in animal toxins acting on ion channels; Biochme. J. 378: 717-726). (Year: 2004).*
Requirement for Restriction for U.S. Appl. No. 15/100,273, dated Nov. 18, 2016, 8 pages.
Response to Requirement for Restriction for U.S. Appl. No. 15/100,273, dated Jan. 18, 2017, 7 pages.
Office Action for U.S. Appl. No. 15/100,273, dated Feb. 17, 2017, 12 pages.
Notice of Abandonment for U.S. Appl. No. 15/100,273, dated Aug. 31, 2017, 2 pages.
International Search Report for international patent application PCT/US14/067,688, dated Feb. 4, 2015, 3 pages.
Written Opinion of International Search Authority for international patent application PCT/US14/067,688, dated Feb. 4, 2015, 5 pages.
International Preliminary Report on Patentability for international patent application PCT/US14/067,688, dated Jun. 7, 2016, 6 pages.
Office Action for U.S. Appl. No. 13/827,906, dated Feb. 13, 2014, 9 pages.
Response to Restriction Requirement for U.S. Appl. No. 13/827,906, dated Mar. 13, 2014, 2 pages.
Office Action for U.S. Appl. No. 13/827,906, dated Aug. 20, 2014, 16 pages.
Amendment and Response to Non-Final Office Action for U.S. Appl. No. 13/827,906, dated Feb. 20, 2015, 15 pages.
Office Action for U.S. Appl. No. 13/827,906, dated Feb. 17, 2016, 16 pages.
Amendment and Response to Final Office Action for U.S. Appl. No. 13/827,906, dated Aug. 15, 2016, 21 pages.
Office Action for U.S. Appl. No. 13/827,906, dated Feb. 27, 2017, 23 pages.
Amendment and Response to Non-Final Office Action for U.S. Appl. No. 13/827,906, dated May 30, 2017, 25 pages.
Office Action for U.S. Appl. No. 13/827,906, dated Nov. 30, 2017, 18 pages.
Amendment and Response to Final Office Action for U.S. Appl. No. 13/827,906, dated May 30, 2018, 18 pages.
Office Action for U.S. Appl. No. 13/827,906, dated Apr. 9, 2019, 21 pages.
Definition of Constituent by Merriam-Webster, dated Aug. 15, 2016 online, 10 pages.
Gao et al. "Modulating Antibacterial Immunity via Bacterial Membrane-Coated Nanoparticles," Nana Lett. 2015, 15, 1403-1409 DOI: 10.1021/nl504798g.
Hu et al. "Nanoparticle biointerfacing by platelet membrane cloaking," Nature, vol. 526, Oct. 1, 2015, p. 118-121 (17 pages) doi:10.1038/nature15373.
Petrov et al. "Toxicity and Immunogenicity of Neisseria meningitidis Lipopolysaccharide Incorporated into Liposomes," Infection and Immunity, Sep. 1992, vol. 60, No. 9, p. 3897-3903.
Yoo et al. "In vitro and in vivo anti-tumor activities of nanoparticles based on doxorubicin-PLGA conjugates," Journal of Controlled Release 68 (2000) 419-431.
Schmitt CK, Meysick KC, O'Brien AD. Bacterial toxins: friends or foes? Emerging infectious diseases 1999, 5(2): 224-234.

Kitchin NR. Review of diphtheria, tetanus and pertussis vaccines in clinical development. Expert Rev Vaccines 2011, 10(5): 605-615.
Greenberg RN, Marbury TC, Foglia G, Wamy M. Phase I dose finding studies of an adjuvanted Clostridium difficile toxoid vaccine. Vaccine 2012, 30(13): 2245-2249.
Mortimer EA, Jr. Immunization against infectious disease. Science 1978, 200(4344): 902-907.
Holmgren J, Svennerholm AM, Lonnroth I, Fall-Persson M, Markman B, Lundbeck H. Development of improved cholera vaccine based on subunit toxoid. Nature 1977, 269(5629): 602-604.
Parish HJ, Cannon DA. Staphylococcal infection: antitoxic immunity. Br Med J 1960, 1(5175): 743-747.
Metz B, Kersten GF, Hoogerhout P, Brugghe HF, Timmermans HA, de Jong A, et al. Identification of formaldehyde-induced modifications in proteins: reactions with model peptides. J Biol Chem 2004, 279(8): 6235-6243.
Cryz SJ, Jr., Furer E, Germanier R. Effect of chemical and heat inactivation on the antigenicity and immunogenicity of Vibrio cholerae. Infect Immun 1982, 38(1): 21-26.
Boes M, Stoppelenburg AJ, Sille FC. Endosomal processing for antigen presentation mediated by CD1 and Class I major histocompatibility complex: roads to display or destruction. Immunology 2009, 127(2): 163-170.
Blum JS, Wearsch PA, Cresswell P. Pathways of antigen processing. Annual review of immunology 2013, 31: 443-473.
Watts C, Powis S. Pathways of antigen processing and presentation. Reviews in immunogenetics 1999, 1(1): 60-74.
Harush-Frenkel O, Debotton N, Benita S, Altschuler Y. Targeting of nanoparticles to the clathrin-mediated endocytic pathway. Biochemical and biophysical research communications 2007, 353(1): 26-32.
Zhang S, Li J, Lykotrafitis G, Bao G, Suresh S. Size-Dependent Endocytosis of Nanoparticles. Advanced materials 2009, 21: 419-424.
Amendment and Response to Non-Final Office Action for U.S. Appl. No. 13/827,906, dated Oct. 17, 2019, 14 pages.
Final Rejection for U.S. Appl. No. 13/827,906, dated Nov. 27, 2020, 16 pages.
Amendement and Response to Final Office Actio for U.S. Appl. No. 13/827,906, dated Apr. 27, 2021, 17 pages.
Fang et al., "Cancer Cell Membrane-Coated Nanoparticles for Anticancer Vaccination and Drug Delivery," Nano Lett. 2014, 14, 2181-2188 dx.doi.org/10.1021/nl500618u.
Gao et al., "Modulating Antibacterial Immunity via Bacterial Membrane-Coated Nanoparticles," Nano Lett. Feb. 11, 2015; 15(2): 1403-1409 doi:10.1021/nl504798g.
Hu et al., "Erythrocyte membrane-camouflaged polymeric nanoparticles as a biomimetic delivery platform," PNAS, Jul. 5, 2011, vol. 108, No. 27, p. 10980-10985 www.pnas.org/cgi/doi/10.1073/pnas.1106634108.
Hu et al., "Nanoparticle biointerfacing via platelet membrane cloaking," Nature, Oct. 1, 2015, 526(7571), 118-121 doi:10.1038/nature15373.
Moore et al., "Specific targeting and delivery of virus envelope-coated nanoparticle cargoes into receptor-bearing cells and subcellular compartments," NSTI-Nanotech, 2007, www.nstiorg, ISBN 1420061836, vol. 2, p. 370-373.
Zhang et al., "Lipid-Polymer Hybrid Nan Op Articles: Synthesis, Characterization and Applications," Nano LIFE, vol. 1, Nos. 1 & 2 (2010) 163-173 doi:10.1142/S179398441000016X.

* cited by examiner

Synthetic Liposomes + Pore-forming toxins = Liposome-bound toxins

*FIGURE 3*

PLGA polymers + Protein toxins →(Double emulsion) Particle-encapsulated toxins

*FIGURE 4*

Red blood cell membrane coated nanoparticle + Linkers for Toxin attachment / Protein toxins = Particle-linked toxins

*FIGURE 5*

TOXOID PREPARATION AND USES THEREOF

I. CROSS REFERENCE TO RELATED APPLICATIONS

This application is a continuation of U.S. patent application Ser. No. 15/100,273, now pending, which is the national phase of PCT application PCT/US2014/067688 having an international filing date of Nov. 26, 2014, which claims priority to U.S. Provisional Patent Application No. 61/910,861, filed on Dec. 2, 2013. The contents of the above-referenced applications are incorporated by reference herein in their entireties for all purposes.

II. FIELD OF THE INVENTION

The present invention relates to toxoid preparations comprising a non-disrupted and/or a non-denatured toxin associated with a particulate vector that minimizes or precludes said toxin from inflicting damage at an action site of said toxin. The present invention also relates to immunogenic compositions or vaccines comprising the toxoid preparations, and the methods of using the toxoid preparations, immunogenic compositions or vaccines.

III. BACKGROUND OF THE INVENTION

Toxins, e.g., bacterial toxins, are soluble factors that alter the normal metabolism of host cells and inflicts adverse effects. These virulent factors are employed by bacteria for pathogenesis and give rise to symptoms in diseases such as diphtheria, whooping cough, cholera, MRSA infection, tetanus, and anthrax[1]. The development of inactive toxins (toxoids) as vaccines has had major impact on public health, as immunity mounted by these detoxified but antigenically active toxoids can effectively remove the pathogenic factors secreted by bacterial[2, 3, 4, 5]. Presently, toxoid preparations rely primarily on denaturation processes that involve heat and chemical denaturation.

Heat and chemical driven toxin denaturation has been applied to several toxin types for vaccine preparation. However, these procedures can be difficult to control, since inadequate denaturation can leave residual toxicity[6]. Extended denaturation, on the other hand, can greatly compromise the toxoid's antigenic presentation, thereby reducing the vaccine's potency[7, 8].

Therefore, what is needed are improved immunogenic compositions, vaccines, and methods use thereof, against the toxins. The present invention addresses these and other related needs in the art.

IV. SUMMARY OF THE INVENTION

In one aspect, the present invention provides for a toxoid preparation, comprising a non-disrupted and/or a non-denatured toxin associated with a particulate vector that minimizes or precludes said toxin from inflicting damage at an action site of said toxin, provided that said toxoid preparation does not comprise a nanoparticle comprising an inner core comprising a non-cellular material, and an outer surface comprising a cellular membrane derived from a cell and a cell membrane inserting toxin, wherein said cell membrane inserting toxin is associated with said cellular membrane without a linker.

In another aspect, the present invention provides for an immunogenic composition comprising an effective amount of the above toxoid preparation.

In still another aspect, the present invention provides for a method for eliciting an immune response to a toxin in a subject comprising administering to said subject an effective amount of the above immunogenic composition.

In yet another aspect, the present invention provides for a vaccine comprising the above immunogenic composition.

In yet another aspect, the present invention provides for a method for protecting a subject against a toxin comprising administering to said subject an effective amount of the above vaccine In yet another aspect, the present invention provides for a use of an effective amount of the above toxoid preparation for the manufacture of an immunogenic composition against the toxin.

In yet another aspect, the present invention provides for a use of an effective amount of the above immunogenic composition for the manufacture of a vaccine for protecting a subject against the toxin.

In some aspects, the prevent disclosure relates to U.S. application Ser. No. 13/827,906, filed Mar. 14, 2013, International Application No. PCT/US2012/039411, filed May 24, 2012 and published as WO 2013/052167 A2 and U.S. provisional application Ser. No. 61/492,626, filed Jun. 2, 2011. The contents of the above applications are incorporated by reference in their entireties.

V. BRIEF DESCRIPTION OF THE DRAWINGS

Those of skill in the art will understand that the drawings, described below, are for illustrative purposes only. The drawings are not intended to limit the scope of the present teachings in any way.

The patent or application file contains at least one drawing executed in color. Copies of this patent or patent application publication with color drawings will be provided by the Office upon request and payment of the necessary fee.

FIG. 1 schematically illustrates toxin virulence mechanisms at their characteristic sites of actions[1].

Figure 2:
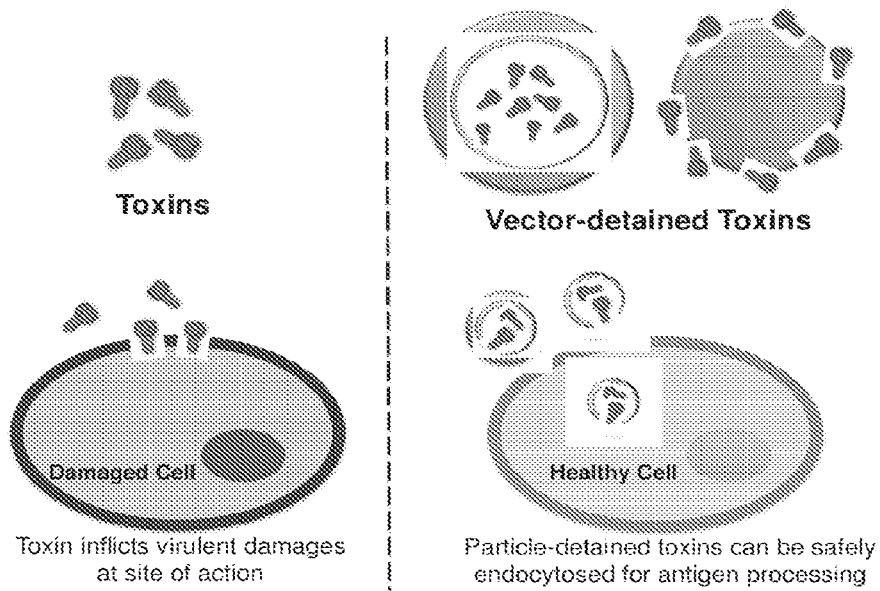

FIG. 2 schematically illustrates exemplary toxin-detainment strategy using particulate vectors to introduce non-disrupted toxin antigens for immune processing. Toxins can be associated with particulate vectors through various means such as encapsulation, electrostatic interactions, and non-specific adsorption, or linker-induced conjugation. The particle/toxin complex can then be endocytosed and preclude toxins from their characteristic sites of actions.

FIG. 3 schematically illustrates a liposome applied for the detainment of pore-forming toxins.

FIG. 4 schematically illustrates polymeric nanoparticle applied for the encapsulation of protein toxins.

FIG. 5 schematically illustrates linking of toxin targets to a red blood cell membrane coated nanoparticle via the aid of synthetic linkers.

VI. DETAILED DESCRIPTION OF THE INVENTION

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, *Molecular Cloning: A Labo-* ratory Manual, 2nd ed. (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds., 1987, and periodic updates); *PCR: The Polymerase Chain Reaction* (Mullis et al., eds., 1994); and Remington, *The Science and Practice of Pharmacy*, 20th ed., (Lippincott, Williams & Wilkins 2003).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Cellular Membrane: The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

In various embodiments, the cellular membrane covering either of the unilamellar or multilamellar nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Viral membrane: As used herein, the term "membrane derived from a virus" refers to viral envelopes that cover the nucleic acid or protein capsids of a virus, and typically contain cellular membrane proteins derived from portions of the host cell membrane (phospholipid and proteins) and include some viral glycoproteins. The viral envelop fuses with the host's membrane, allowing the capside and viral genome to enter and infect the host.

Nanoparticle: The term "nanoparticle" as used herein refers to nanostructure, particles, vesicles, or fragments thereof having at least one dimension (e.g., height, length, width, or diameter) of between about 1 nm and about 10 µm. For systemic use, an average diameter of about 50 nm to about 500 nm, or 100 nm to 250 nm may be preferred. The term "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. In some embodiments, the nanoparticle consisting an inner core covered by an outer surface comprising the membrane as discussed herein. The invention contemplates any nanoparticles now known and later developed that can be coated with the membrane described herein.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of a compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosul fates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which a compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20'" ed., (Lippincott, Williams & Wilkins 2003). Except insofar as any conventional media or agent is incompatible with the active compound, such use in the compositions is contemplated.

Phospholipid: The term "phospholipid", as used herein, refers to any of numerous lipids contain a diglyceride, a phosphate group, and a simple organic molecule such as choline. Examples of phospholipids include, but are not limited to, Phosphatide acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP), Phosphatidylinositol bisphosphate (PIP2) and Phosphatidylinositol triphosphate (P1P3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as an infection or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

Vaccine: a composition capable of eliciting in a patient a beneficial active or passive immune response to a specific antigen. While protective immunity may be desired, it is understood that various levels of temporal immune response can be beneficial.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The term "combination" refers to either a fixed combination in one dosage unit form, or a kit of parts for the combined administration where a compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. Toxoid Preparations

In one aspect, the present invention provides for a toxoid preparation, comprising a non-disrupted and/or a non-denatured toxin associated with a particulate vector that minimizes or precludes said toxin from inflicting damage at an action site of said toxin, provided that said toxoid preparation does not comprise a nanoparticle comprising an inner core comprising a non-cellular material, and an outer surface comprising a cellular membrane derived from a cell and a cell membrane inserting toxin, wherein said cell membrane inserting toxin is associated with said cellular membrane without a linker.

The present toxoid preparation can comprise any suitable type of toxin. As used herein, the "toxin" refers to a toxic material or product of plants, animals, microorganisms (including, but not limited to, bacteria, vims, fungi, rickettsiae or protozoa), or infectious substances, or a recombinant or synthesized molecule, whatever their origin and method of production. In certain embodiment, the "toxin" includes a bacterial, fungal, or animal toxin that is produced within living cells or organisms.

In certain embodiments, the bacterial toxin includes exotoxin and endotoxin. As used herein, "exotoxins" are generated by the bacteria and actively secreted, while "endotoxins" are part of the bacteria itself (e.g., bacterial outer membrane), and it is not released until the bacteria is killed by the immune system. The present invention contemplates any exotoxin and endotoxin now known and later discovered. The type of bacterial toxin inserted in the cellular membrane is not particularly limited. In certain embodiments, the bacterial toxin is a cell membrane inserting toxin from S. aureus, such as alpha-hemolysin.

The present invention further contemplates any fungal toxins now known and later discovered, including but not limited to, aflatoxin, citrinin, ergotamine, fumonisins, ergovaline, ochratoxin, phomopsin, slaframine, sporidesmin, trichothecenes (e.g., satratoxin, deoxynivalenol), zearalenone. The type of fungal toxin inserted in the cellular membrane is not particularly limited.

The animal toxins contemplated in the present invention include any poison substances produced by an animal. Examples of animal toxins include, but are not limited to, cardiovascular toxins, gastrointestinal toxins respiratory toxin, neurological toxins, kidney/organ failure toxins. The present invention contemplates any animal toxins now known and later discovered, and the type of animal toxin inserted in the cellular membrane is not particularly limited. In certain embodiments, an animal toxin inserting into the cell membrane is from an arthropod such as the insects, arachnids and crustaceans or a reptile such as crocodilia, rhynchocephalia, squamata (including lizards and snakes) and testudines.

In some embodiments, the present toxoid preparation comprises a pore-forming toxin, an inhibitory toxin, a toxin interacts with a cellular receptor or secondary messenger to disrupt normal cellular metabolism, a neurotoxin, and an enterotoxin. An exemplary pore-forming toxin is alpha hemolysin of Staphylococcus aureus. An exemplary inhibitory toxin is Shiga toxin. An exemplary inhibitory toxin interacts with a cellular receptor or secondary messenger is Cholera toxin.

The toxin can be associated with the particulate vector by any suitable means or methods. For example, the toxin can be associated with the particulate vector via encapsulation, electrostatic absorption, non-specific interaction, and/or structure-specific association.

In some embodiments, the particulate vector can be configured to facilitate endocytic uptake of the toxoid preparation and/or to minimize or prevent premature toxin release from the toxoid preparation.

In some embodiments, the particulate vector can be configured to allow the toxin to be processed in an endolysosomal compartment.

In some embodiments, an exemplary toxoid preparation comprises a lipoplex comprising synthetic lipid bilayers and an absorbed membrane-affinity toxin. The membrane-affinity toxin can be any suitable toxin, e.g., a pore forming toxin. The lipoplex can comprise any suitable synthetic lipid, such as phosphotidylcholine, phosphotidylethanolamine, phosphatidylinositol, phosphotidylserine, and sphingomylin. The lipoplex can exist in any suitable form. For example, the lipoplex can be a liposome or a lipid-coated nanoparticle.

In some embodiments, an exemplary toxoid preparation comprises a solid nanoparticle that encapsulates a toxin. Any suitable solid nanoparticle can be used. Exemplary solid nanoparticle includes a polymeric nanoparticle, a lipid coated nanoparticle, a silica nanoparticle, a calcium-based nanoparticle, a dendrimer, and a gold nanoparticle. In some embodiments, the polymeric nanoparticle can be a biodegradable polymeric nanoparticle. In other embodiments, the biodegradable polymeric nanoparticle comprises poly(lactic-co-glycolic acid) (PLGA) and encapsulates a soluble polypeptide toxin.

In some embodiments, an exemplary toxoid preparation comprises a cellular membrane-coated nanoparticle or a biomembrane-derived particle and a toxin associated with the cellular membrane-coated nanoparticle or the biomembrane-derived particle via a linker. Any suitable cellular membrane-coated nanoparticle or a biomembrane-derived particle can be used.

In some embodiments, the cellular membrane can comprise a plasma membrane or an intracellular membrane. In other embodiments, the cellular membrane can be derived from a unicellular organism such as a bacterium and a fungus, or a multicellular organism such as a plant, a vertebrate, a non-human mammal, and a human. In still other embodiments, the cellular membrane can be derived from a blood cell, a tumor cell, a cancer cell, an immune cell, a stem cell, an endothelial cell, an exosome, a secretory vesicle or a synaptic vesicle. In yet other embodiments, the cellular membrane can comprise a plasma membrane derived from a red blood cell.

Any suitable linker can be used. For example, a linker can comprise a lipid anchor for the cellular membrane, e.g., a plasma membrane derived from a red blood cell, and a chemical moiety for covalent or non-covalent conjugation to the toxin.

In some embodiments, the particulate vector can comprise an inner core comprising a non-cellular material. Any non-cellular material can be used. In certain embodiments, the inner core supports the outer surface and comprises a biocompatible or a synthetic material. Examples of the biocompatible or a synthetic material include, but are not limited to, poly(lactic-co-glycolic acid) (PLGA), polylactic acid (PLA), polyglycolic acid (PGA), polycaprolactone (PCL), polylysine, polyglutamic acid, and any other biocompatible or synthetic material that are suitable. The present invention contemplates any biocompatible or synthetic material, now known or later developed, that can be used in the inner core of the particulate vector, and the type of such material is not particularly limited.

In some embodiments, the particulate vector contained in the toxoid preparation is biodegradable.

The particulate vector can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

The particulate vector can have any suitable size or diameter. For example, the diameter of the particulate vector can be from about 10 nm to about 10 μm. In certain embodiments, the diameter of the particulate vector in the toxoid preparation is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm.

In yet another aspect, the present invention provides for a use of an effective amount of the above toxoid preparation for the manufacture of an immunogenic composition against the toxin.

C. Immunogenic Compositions, Vaccines and Methods Using Thereof

In another aspect, the present invention provides for an immunogenic composition comprising an effective amount of the toxoid preparation descried above, e.g., in the Summary of the Invention and the above Section V.B.

In some embodiments, the particulate vector in the toxoid preparation substantially retains the toxin. For example, the particulate vector can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the toxin.

In some embodiments, the toxin in the toxoid preparation substantially retains its natural structural integrity for eliciting an immune response to a natural toxin. For example, the toxin in the toxoid preparation can retain at 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for eliciting an immune response to a natural toxin. In another example, the toxin in the toxoid preparation can be used to elicit an immune response that is the same, or substantially the same or equivalent to an immune response elicited by a natural toxin under the same or similar conditions and/or from the same or same type of the subject. As used herein, the structural integrity of the toxin includes primary, secondary, tertiary and/or quaternary structure of the toxin as contained in the toxoid preparation.

The present immunogenic composition can comprise any suitable type of toxin. As used herein, the "toxin" refers to a toxic material or product of plants, animals, microorganisms (including, but not limited to, bacteria, vims, fungi, rickettsiae or protozoa), or infectious substances, or a recombinant or synthesized molecule, whatever their origin and method of production. In certain embodiment, the "toxin" includes a bacterial, fungal, or animal toxin that is produced within living cells or organisms.

In certain embodiments, the bacterial toxin includes exotoxin and endotoxin. As used herein, "exotoxins" are generated by the bacteria and actively secreted, while "endotoxins" are part of the bacteria itself (e.g., bacterial outer membrane), and it is not released until the bacteria is killed by the immune system. The present invention contemplates any exotoxin and endotoxin now known and later discovered. The type of bacterial toxin inserted in the cellular membrane is not particularly limited. In certain embodiments, the bacterial toxin is a cell membrane inserting toxin from *S. aureus*, such as alpha-hemolysin.

The present invention further contemplates any fungal toxins now known and later discovered, including but not limited to, aflatoxin, citrinin, ergotamine, fumonisins, ergovaline, ochratoxin, phomopsin, slaframine, sporidesmin, trichothecenes (e.g., satratoxin, deoxynivalenol), zearalenone. The type of fungal toxin inserted in the cellular membrane is not particularly limited.

The animal toxins contemplated in the present invention include any poison substances produced by an animal. Examples of animal toxins include, but are not limited to, cardiovascular toxins, gastrointestinal toxins respiratory toxin, neurological toxins, kidney/organ failure toxins. The present invention contemplates any animal toxins now known and later discovered, and the type of animal toxin inserted in the cellular membrane is not particularly limited. In certain embodiments, die animal toxin inserting into the cell membrane is from an arthropod such as the insects, arachnids and crustaceans or a reptile such as crocodilia, rhynchocephalia, squamata (including lizards and snakes) and testudines.

In some embodiments, the present immunogenic composition comprises a pore-forming toxin, an inhibitory toxin, a toxin interacts with a cellular receptor or secondary messenger to disrupt normal cellular metabolism, a neurotoxin, and an enterotoxin. An exemplary pore-forming toxin is alpha hemolysin of *Staphylococcus aureus*. An exemplary inhibitory toxin is Shiga toxin. An exemplary inhibitory toxin interacts with a cellular receptor or secondary messenger is Cholera toxin. In some embodiments, the present immunogenic composition comprises a bacterial, fungal, or animal toxin.

The present immunogenic composition can comprise any suitable additional substance. For example, the present immunogenic composition can further comprise another active ingredient, an immunogenic adjuvant, and/or an immunopotentiator. As used herein, the "immunogenic adjuvant" is a substance or composition which can induce and/or enhance an immune response against an antigen. As used herein, the "immunopotentiator" refers to an agent that on inoculation enhances the immune response. The present invention contemplates any suitable immunogenic adjuvant or immunopotentiator now known or later developed, and the type of the immunogenic adjuvant or immunopotentiator used along with or in combination with present immunogenic composition is not particularly limited. Exemplary immunogenic adjuvant can be Freund's complete adjuvant which is a mixture of light mineral oil, Arlacel detergent, and inactivated *Mycobacterium tuberculosis* bacilli. Exemplary immunopotentiator includes Bacille Calmette-Guerin (BCG), *Corynebacterium parvum, Brucella abortus* extract, glucan, levamisole, tilorone, an enzyme and a non-virulent virus.

In still another aspect, the present invention provides for a method for eliciting an immune response to a toxin in a subject comprising administering to said subject an effective amount of the above immunogenic composition.

In yet another aspect, the present invention provides for a vaccine comprising the above immunogenic composition. The present vaccine can be used in any suitable manner. For example, the present vaccine can be administered into a target tissue of a subject including human to induce a protective immune response in the living body of the subject.

In yet another aspect, the present invention provides for a method for protecting a subject against a toxin comprising administering to said subject an effective amount of the above vaccine.

The present methods can be used to protect a subject against any suitable toxin. As used herein, the "toxin" refers to a toxic material or product of plants, animals, microorganisms (including, but not limited to, bacteria, vims, fungi, rickettsiae or protozoa), or infectious substances, or a recombinant or synthesized molecule, whatever their origin and method of production. In certain embodiment, the "toxin" includes a bacterial, fungal, or animal toxin that is produced within living cells or organisms.

In certain embodiments, the bacterial toxin includes exotoxin and endotoxin. As used herein, "exotoxins" are generated by the bacteria and actively secreted, while "endotoxins" are part of the bacteria itself (e.g., bacterial outer membrane), and it is not released until the bacteria is killed by the immune system. The present invention contemplates any exotoxin and endotoxin now known and later discovered. The type of bacterial toxin inserted in the cellular membrane is not particularly limited. In certain embodiments, the bacterial toxin is a cell membrane inserting toxin from *S. aureus*, such as alpha-hemolysin.

The present invention further contemplates any fungal toxins now known and later discovered, including but not limited to, aflatoxin, citrinin, ergotamine, fumonisins, ergovaline, ochratoxin, phomopsin, slaframine, sporidesmin, trichothecenes (e.g., satratoxin, deoxynivalenol), zearalenone. The type of fungal toxin inserted in the cellular membrane is not particularly limited.

The animal toxins contemplated in the present invention include any poison substances produced by an animal. Examples of animal toxins include, but are not limited to, cardiovascular toxins, gastrointestinal toxins respiratory toxin, neurological toxins, kidney/organ failure toxins. The present invention contemplates any animal toxins now known and later discovered, and the type of animal toxin inserted in the cellular membrane is not particularly limited. In certain embodiments, die animal toxin inserting into the cell membrane is from an arthropod such as the insects, arachnids and crustaceans or a reptile such as crocodilia, rhynchocephalia, squamata (including lizards and snakes) and testudines.

In some embodiments, the present methods can be used to protect a subject against a pore-forming toxin, an inhibitory toxin, a toxin interacts with a cellular receptor or secondary messenger to disrupt normal cellular metabolism, a neurotoxin, and an enterotoxin. An exemplary pore-forming toxin is alpha hemolysin of *Staphylococcus aureus*. An exemplary inhibitory toxin is Shiga toxin. An exemplary inhibitory toxin interacts with a cellular receptor or secondary messenger is Cholera toxin. In some embodiments, the toxin is a bacterial, fungal, or animal toxin.

The present methods can be used to protect any suitable subject. For example, the present methods can be used to protect a human or a non-human mammal.

The present methods can use a vaccine that comprises any suitable toxoid preparation. In some embodiments, the toxoid preparation comprises a cellular membrane-coated nanoparticle and a toxin associated with the cellular membrane-coated nanoparticle via a linker, and the cellular membrane is derived from a cell of the same species of the subject or a cell of the subject. Any cellular membrane can be used in the toxoid preparation. For example, the cellular membrane can be derived from a red blood cell of the same species of the subject and the red blood cell has the same blood type of the subject.

The present methods can further comprise administering another active ingredient or a pharmaceutically acceptable carrier or excipient to said subject.

The present methods can be used to elicit any suitable immune response. For example, the present methods can be used to elicit a T-cell mediated immune response, or a B-cell mediated immune response.

The present invention further provides administering to the subject in need one or more other active ingredient, with or without a pharmaceutically acceptable carrier or excipient, along or in combination with the aforementioned immunogenic composition or vaccine. The aforementioned immunogenic composition or the vaccine of the present invention, as well as the other active ingredient, can be administered, alone or in combination, via any suitable administration route, including but not limited to oral, nasal, inhalational, parental, intravenous, intraperitoneal, subcutaneous, intramuscular, intradermal, topical, or rectal. In certain embodiments, the immunogenic composition or the vaccine of the present invention, as well as the other active ingredient, is administered via a medicament delivery system to the subject in need. The type of administration route or the type of other active ingredient used herein are not particularly limited.

In yet another aspect, the present invention provides for a use of an effective amount of the above immunogenic composition for the manufacture of a vaccine for protecting a subject against the toxin.

VII. EXEMPLARY EMBODIMENTS

Many different types of bacterial toxins exist, and each type of toxin has distinctive site of action where it can exert its virulence effect. FIG. 1 depicts three primary toxin categories and illustrates their specific site of action with regards to their target cells. In the first category, membrane-damaging toxins (i.e., alpha hemolysin of *Staphylococcus aureus*) interact with cellular membranes and form membrane pores that disrupt ion regulation. In the second category, inhibitory toxins (i.e., Shiga toxin) can interact with molecular machineries and disrupt protein synthesis. In the third category, toxins interact with receptors or other secondary messengers to disrupt normal cellular metabolism (i.e., Cholera toxin)[1]. These virulence actions typically take place at characteristic sites of actions, such as at the exoplasmic face of cellular surfaces, within the cellular membranes, or inside the cytosol. Such virulence actions can be obviated if the toxins are to be precluded from their respective site of action. A vaccine vector that can reroute toxins from their site of action (i.e., cellular membranes, cytosol, or exoplasmic receptors) can therefore deliver non-denatured toxins for immune processing.

Central to our body's ability to mount immune responses to vaccines is the process of antigen-processing by antigen-presenting cells. The primary location that antigen-processing is inside endosomes and lysomes[9, 10, 11], where proteins are degraded by acid-depend proteases. Many particulate vectors are known to be readily uptaken by cells through the endocytic pathway[12, 13].

In some embodiments, the present disclosure, therefore, describes a novel toxoid preparation process wherein a non-disrupted, non-denatured toxin is associated with a particulate vector that precludes the toxin from inflicting damages at their characteristic site of action. By shuttling toxins to the endolysosomal compartments, such vector-based toxoid allows antigenically persevered toxins to be safely processed (FIG. 2). In principle, toxin detainment by particulate vectors can be achieved by methods including but not limited to encapsulation, electrostatic absorption, and non-specific interaction, and structure-specific association. Particulate vectors can be designed to facilitate the particle's endocytic uptake and minimizes premature toxin release. Toxin associated with the particulate vector can then directed away from their site of action and faithfully present their antigenic information for immune process. Such vaccine design can be more potent than conventional toxoid that are denatured and can be applied to multiple toxin types with known characteristic site of action, including but not limited to pore-forming toxins, neurotoxins, and enterotoxins.

In one embodiment, a lipoplex comprising or consisting of synthetic lipid bilayers are used to absorb a membrane-affinity toxin such as a pore forming toxin. Association of the toxin with the particulate vector enables the endocytic uptake of the complex. The resulting toxoid formulation can be safely delivered and is capable of mounting a more potent humoral response as compared to heat-denatured toxoid (FIG. 3). Synthetic lipids used for liposome preparation include but are not limited to phosphotidylcholine, phosphotidylethanolamine, phosphatidylinositol, phosphotidylserine, and sphingomylin. The lipoplex can be any lipid-based particulate vector including but not limited to liposomes and lipid-coated nanoparticles.

In another embodiment, a solid nanoparticles is used to encapsulate a toxin, e.g., a protein toxin, to deliver them for antigen processing. A biodegradable polymeric nanoparticle comprising or consisting of PLGA is applied to encapsulate soluble protein antigens through a w/o/w double emulsion process (FIG. 4). Toxins enclosed within nanoparticles are precluded from their virulence targets. Particulate vectors used to encapsulate toxins include but are not limited to polymeric nanoparticle, lipid coated nanoparticles, silica nanoparticles, or nanoemulsions.

In a third embodiment, a linker is used to associate a toxin, e.g., a soluble toxin, to a red blood cell membrane-coated nanoparticle (FIG. 5). The linker constrains the toxin from inflicting its virulence effect and the resulting vector-based toxoid can be endocytosed for antigen processing. In the particular example, the linker possesses a lipid anchor for RBC membrane insertion and a chemical linker for covalent conjugation to toxins. The linker can be of any configuration with bipolar affinity, where one side of the linker has affinity to particulate vectors and the other side has affinity to toxin targets. The particle vectors include but are not limited to biomembrane-derived particles, synthetic liposomes, polymeric nanoparticle, silica nanoparticles, silica nanoparticles, and gold nanoparticles.

VIII. REFERENCES

1. Schmitt C K, Meysick K C, O'Brien A D. Bacterial toxins: friends or foes? *Emerging infectious diseases* 1999, 5(2): 224-234.
2. Kitchin N R. Review of diphtheria, tetanus and pertussis vaccines in clinical development. *Expert Rev Vaccines* 2011, 10(5): 605-615.
3. Greenberg R N, Marbury T C, Foglia G, Warny M. Phase I dose finding studies of an adjuvanted *Clostridium difficile* toxoid vaccine. *Vaccine* 2012, 30(13): 2245-2249.
4. Mortimer E A, Jr. Immunization against infectious disease. *Science* 1978, 200(4344): 902-907.
5. Holmgren J, Svennerholm A M, Lonnroth I, Fall-Persson M, Markman B, Lundbeck H. Development of improved cholera vaccine based on subunit toxoid. *Nature* 1977, 269(5629): 602-604.
6. Parish H J, Cannon D A. Staphylococcal infection: antitoxic immunity. *Br Med J* 1960, 1(5175): 743-747.

7. Metz B, Kersten G F, Hoogerhout P, Brugghe H F, Timmermans H A, de Jong A, et al. Identification of formaldehyde-induced modifications in proteins: reactions with model peptides. *J Biol Chem* 2004, 279(8): 6235-6243.
8. Cryz S J, Jr., Furer E, Germanier R. Effect of chemical and heat inactivation on the antigenicity and immunogenicity of *Vibrio cholerae*. *Infect Immun* 1982, 38(1): 21-26.
9. Boes M, Stoppelenburg A J, Sille F C. Endosomal processing for antigen presentation mediated by CD1 and Class I major histocompatibility complex: roads to display or destruction. *Immunology* 2009, 127(2): 163-170.
10. Blum J S, Wearsch P A, Cresswell P. Pathways of antigen processing. *Annual review of immunology* 2013, 31: 443-473.
11. Watts C, Powis S. Pathways of antigen processing and presentation. *Reviews in immunogenetics* 1999, 1(1): 60-74.
12. Harush-Frenkel O, Debotton N, Benita S, Altschuler Y. Targeting of nanoparticles to the clathrin-mediated endocytic pathway. *Biochemical and biophysical research communications* 2007, 353(1): 26-32.
13. Zhang S, Li J, Lykotrafitis G, Bao G, Suresh S. Size-Dependent Endocytosis of Nanoparticles. *Advanced materials* 2009, 21: 419-424.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. An immunogenic composition comprising an effective amount of a liposome and an immunogenic adjuvant or immunopotentiator, and wherein said liposome comprises synthetic lipid bilayers and a pore-forming toxin absorbed in said synthetic lipid bilayers of said liposome, wherein:

said synthetic lipid bilayers comprise sphingomyelin, said pore-forming toxin is alpha hemolysin of *Staphylococcus aureus* or an animal pore-forming toxin, said synthetic lipid bilayers further comprise a synthetic lipid that is selected from the group consisting of phosphotidylcholine, phosphotidylethanolamine, phosphatidylinositol and phosphotidylserine, said liposome has at least one dimension between about 1 nm and about 150 nm, said liposome does not comprise a solid inner core, and said pore-forming toxin substantially retains its natural structural integrity for eliciting an immune response to a natural pore-forming toxin.

2. The immunogenic composition of claim 1, wherein the liposome substantially retains the pore-forming toxin.

3. The immunogenic composition of claim 1, wherein the pore-forming toxin is alpha hemolysin of *Staphylococcus aureus*.

4. The immunogenic composition of claim 1, further comprising another active ingredient.

5. A vaccine comprising the immunogenic composition of claim 1.

6. The immunogenic composition of claim 1, wherein the liposome is configured to allow the pore-forming toxin to be processed in an endolysosomal compartment.

7. The immunogenic composition of claim 1, wherein the synthetic lipid bilayers comprise a synthetic lipid that is selected from the group consisting of phosphotidylethanolamine, phosphatidylinositol, and phosphotidylserine.

* * * * *